United States Patent

Hawkes et al.

[11] Patent Number: 5,972,637
[45] Date of Patent: Oct. 26, 1999

[54] DETERMINING THE ORGANIC CONTENT OF A FLUID

[75] Inventors: Dennis Hawkes; Freda Hawkes, both of Cardiff; Richard Mark Dinsdale, Leyburn, all of United Kingdom

[73] Assignee: University of Glamorgan Commercial Services Limited, Pontypridd, United Kingdom

[21] Appl. No.: 09/235,453

[22] Filed: Jan. 22, 1999

Related U.S. Application Data

[63] Continuation of application No. 08/860,108, Jun. 16, 1997, Pat. No. 5,863,749.

[30] Foreign Application Priority Data

Dec. 16, 1994 [GB] United Kingdom ............... 9425408
May 24, 1995 [GB] United Kingdom ............... 9510513

[51] Int. Cl.$^6$ ............... C12Q 1/28; C12Q 1/32; C12Q 1/00
[52] U.S. Cl. ............... 435/28; 435/26; 435/25; 435/27; 435/4; 436/62; 436/63
[58] Field of Search ............... 435/28, 26, 25, 435/27, 4; 436/62, 63

[56] References Cited

U.S. PATENT DOCUMENTS

| | | | |
|---|---|---|---|
| 3,926,732 | 12/1975 | Rosen et al. | 435/28 |
| 4,153,510 | 5/1979 | Messing et al. | 435/28 |
| 4,202,938 | 5/1980 | Haeckel et al. | 435/28 |
| 4,338,399 | 7/1982 | Weil et al. | 435/28 |
| 4,356,092 | 10/1982 | Shimizu et al. | 435/28 |
| 4,414,334 | 11/1983 | Hitzman | 435/28 |
| 4,663,044 | 5/1987 | Goronszy | 435/28 |
| 4,765,901 | 8/1988 | Field | 435/28 |
| 5,098,830 | 3/1992 | Bar-or et al. | 435/28 |
| 5,863,749 | 1/1999 | Hawkes et al. | 435/28 |

FOREIGN PATENT DOCUMENTS

| | | |
|---|---|---|
| 0053865 | 6/1982 | European Pat. Off. |
| 0181210 | 5/1986 | European Pat. Off. |

*Primary Examiner*—Louise N. Leary
*Attorney, Agent, or Firm*—Vinson & Elkins L.L.P.

[57] ABSTRACT

The organic content of a fluid is determined by: (a) reacting a sample of a fluid containing organic matter (such as viable biomass or soluble or insoluble organic compounds) with excess oxidizing agent; (b) permitting an enzyme catalyzed release of oxygen from any unreacted oxidizing agent; and (c) measuring the volume of oxygen liberated from the sample; wherein the volume of oxygen liberated provides a measure of the organic content of the fluid.

20 Claims, 1 Drawing Sheet

DETERMINING THE ORGANIC CONTENT OF A FLUID

RELATED APPLICATIONS

This application is a continuation of U.S. patent application No. 08/860,108, filed Jun. 16, 1997, also entitled "DETERMINING THE ORGANIC CONTENT OF A FLUID", which issued as U.S. Pat. No. 5,863,749 on Jan. 26, 1999.

TECHNICAL FIELD OF THE INVENTION

The present invention is concerned with a method of determining the organic content (such as, for example, the biomass content) of a fluid; in particular the invention is concerned with a method of determining the organic content of a fluid which may be operated in a continuous process.

BACKGROUND OF THE INVENTION

Frequently, in industrial waste treatment, waste water treatment or in brewing plants or the like, an accurate measurement of the organic content of a fluid may be required so as to determine, for example, the treatment or filtration efficiency of the plant. Typically, any such measurements are taken only once during the working day, which is insufficient to identify fluctuating organic loads within the fluid, thus leading to inefficient treatment of the fluid due because of use of non-optimal conditions for treatment of the fluid.

Furthermore, waste water of both domestic and industrial origin is frequently treated by a biological aerobic process which uses suspended micro-organisms (the activated sludge process). The biomass concentration is an important parameter in maintaining effluent quality. It is generally measured off-line as dry weight. On-line probes based on, for example, turbidity, are generally unreliable and measure inert particles and dead cells.

SUMMARY OF THE INVENTION

We have now developed a method of determining the organic content of a fluid, which can be used for organic compounds for biomass, and which can provide more effective monitoring and process control and hence optimization of the treatment process.

Thus, according to the present invention there is provided a method of determining the content of organic matter of a fluid (generally in aqueous fluid), which method comprises:

(a) reacting a sample of the fluid with an oxidizing agent;

(b) permitting enzyme catalyzed release of oxygen from unreacted oxidizing agent; and (c) measuring the volume of oxygen liberated from the sample; wherein the volume of oxygen liberated provides a measure of the content of organic matter of the fluid.

The volume may be measured as an absolute volume, or as a rate of evolution (in other words, the volume evolved in a unit time).

BRIEF DESCRIPTION OF THE DRAWINGS

Exemplary embodiments of the invention will be more clearly described with reference to the accompanying drawing by way of example only, wherein.

DESCRIPTION OF THE PREFERRED EMBODIMENTS

Figure 1:
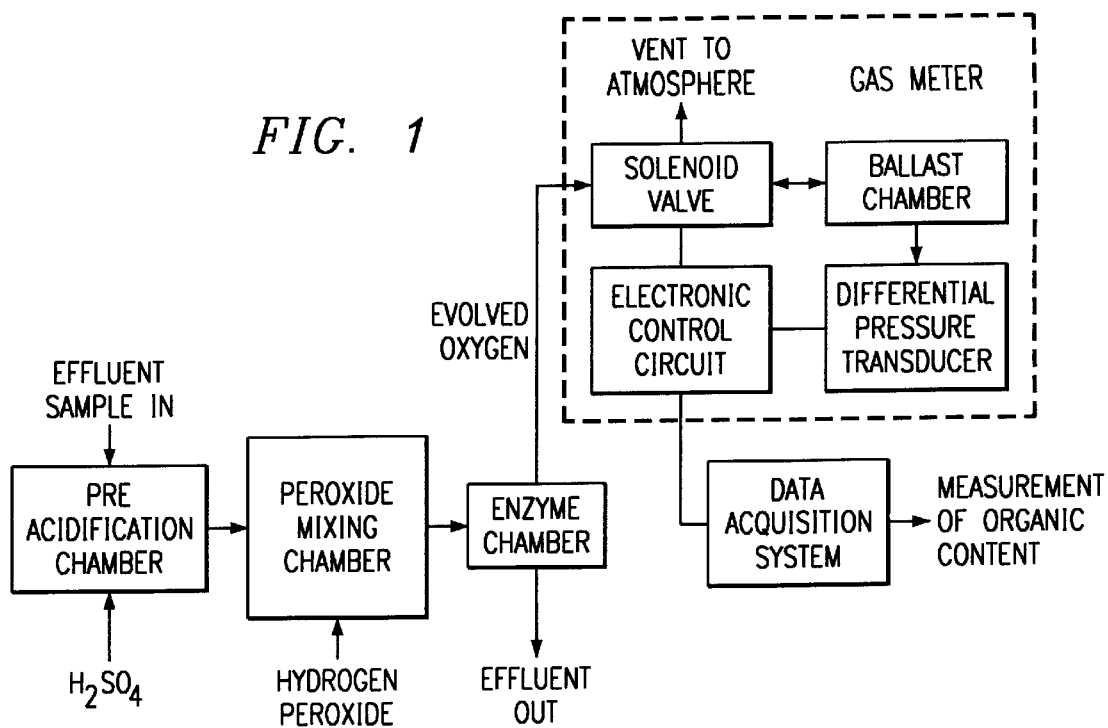
FIG. 1 is a schematic diagram of one embodiment of the invention.

In one embodiment of the invention the method may be used to provide a measure of the living or viable biomass content of a fluid, such as for example, the content of active aerobic cells in a sample of fluid. Thus, advantageously, the method can be used to determine the amount of microbes present in, for example, aerobic biotreatment processes. In this embodiment the fluid may be subjected to chemical or physical treatment to disrupt the cells, either prior to, or co-incident with, step (a); it is not necessary for the oxidizing agent to be in excess.

In further embodiments (such as when the organic matter comprises soluble or insoluble organic compounds, such as hydrocarbons or cellulose present in the fluid), the oxidizing agent is present in excess relative to the organic matter. In this embodiment, the reaction of the sample with excess oxidizing agent causes organic material contained in the fluid to be oxidized, and residual unreacted oxidizing agent, when reacted with the enzyme, releases oxygen from the oxidizing agent which may then be measured. The volume of oxygen liberated provides a measure of the content of organic matter of the fluid, because the volume of oxygen liberated is substantially inversely proportional to the volume of organic matter in the sample.

In this embodiment of the invention, the method may be used to determine the organic content of a fluid, such as the organic load of effluent in, for example, waste water treatment plants or the like. In this embodiment, the resulting mixture from step (a) is contacted with an immobilized enzyme, capable of releasing oxygen from any unreacted oxidizing agent.

In this embodiment of the invention, the oxidizing agent is, preferably, reacted with the sample of fluid separate from the immobilized enzyme for sufficient time to oxidize substantially all of the organic matter present. The sample of fluid is, preferably, acidified prior to reaction with the oxidizing agent. Thus, advantageously, the fluid can be kept at a pH sufficient to inhibit activity of any micro-organisms present which may possess peroxidase activity.

The sample may also be subjected to further treatment prior to oxidation, such as homogenization, or heat treatment or both. The temperature of the process may be kept at a temperature not substantially less than biological temperature, or, alternatively, the fluid may be heated so as to further inhibit any peroxidase activity of micro-organisms, and also to increase the oxidizing ability of the oxidizing agent.

Preferably the oxygen liberated may be measured using a pressure transducer or the like such as a low-flow gas meter. Thus, the organic content of the sample at any given time may be determined, for example, in a continuous treatment process.

Preferably the oxidizing agent to be used in each of the embodiments is hydrogen peroxide, typically in liquid form, which advantageously, is easy to handle and relatively inexpensive for large industrial scale use.

The amount of hydrogen peroxide to be used in the first embodiment (where the organic matter comprises non-viable organic compounds), which hydrogen peroxide is in excess of the organic matter in the sample, may be determined using a feedback mechanism. The feedback mechanism may comprise reacting a sample of the fluid with hydrogen peroxide in the method according to the invention, and measuring the volume of oxygen liberated. Increasing amounts of hydrogen peroxide may be reacted with the sample until such time as oxygen is liberated following reaction with the enzyme; this is indicative of excess oxidizing agent.

Preferably, the enzyme used in each of the embodiments is a peroxidase or catalase. Thus, advantageously, where the method is used for determining viable or living biomass, the catalase is one naturally present in the cells.

Preferably, the measurements by the gas meter of the oxygen liberated from the sample are passed to a data acquisition system for processing, where, advantageously, the information may be calibrated to produce an accurate reading of the organic matter present.

The method according to the invention may be used in a wide range of industrial applications such as in waste water treatment or brewing.

The method also allows continuous monitoring of microorganisms present, in for example, aerobic biotreatment processes, or monitoring of receiving waters.

The efficiency of a treatment process may be determined by monitoring the organic content of the fluid prior to the treatment process using the method according to the invention and comparing the readings obtained with readings of the organic content of the fluid obtained after the treatment process.

Preferably, the data acquisition system provides for a feed-back mechanism to selectively control the treatment process, thus ensuring optimization of the treatment conditions of the fluid. In one embodiment, substantially the whole process may be controlled by a microprocessor, or the like. Thus, advantageously, the treatment and monitoring processes may be automatic.

Figure 2:
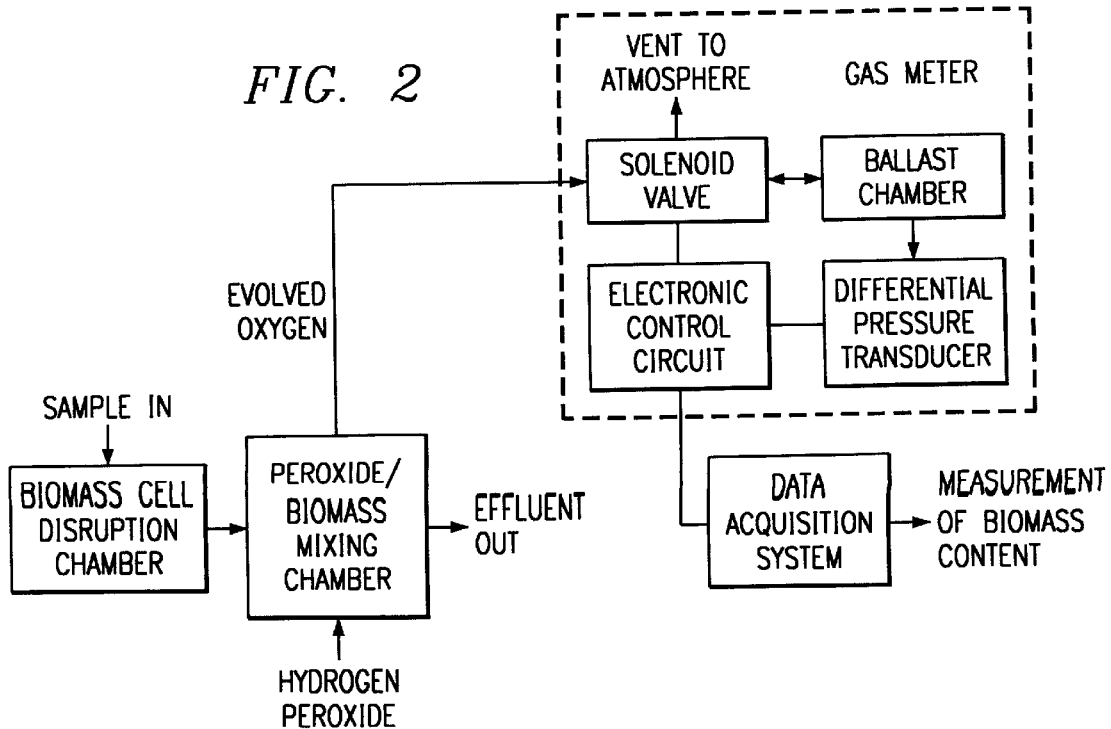
FIG. 2 is a schematic diagram of an alternative embodiment of the invention.

Referring to FIG. 1, there is illustrated a method of determining the organic content of a fluid which consists of adding to a pre-acidified fluid sample, an excess of oxidizing hydrogen peroxide in a first mixing chamber and passing the fluid, containing residual hydrogen peroxide, to a chamber for reaction with an immobilized enzyme, such as a catalase or a peroxidase, in order to liberate the oxygen of the residual hydrogen peroxide. Measurements of the liberated oxygen are then taken by a low flow gas meter, and the information passed to a data acquisition system or microprocessor unit controlling the treatment process and which determines the organic load of the fluid sample. The microprocessor then ensures any necessary adjustments of the treatment conditions to be applied to the fluid to ensure optimum treatment conditions for the fluid which may contain a fluctuating organic load.

Where the biomass content of a fluid is to be measured, the method used is that shown in FIG. 2. A sample of the fluid is passed into a chamber where the integrity of the cells is disrupted. The cells then pass into another reaction chamber where a constant supply of hydrogen peroxide is introduced. Chemical or physical treatments can be used to disrupt the cells. This can be coincident with the hydrogen peroxide mixing stage or, as above, in a prior treatment step. The catalase which is naturally present in the aerobic cells catalyzes the release of oxygen from the hydrogen peroxide added. The rate of flow of oxygen liberated represents a measurement of the viable aerobic or facultative biomass in the sample. Measurements of the liberated oxygen are taken by a low flow gas meter, as described above.

We claim:

1. A method of monitoring the reaction of organic matter with an oxidizing agent, comprising the steps of:
    (a) treating a sample of fluid containing said organic matter with an oxidizing agent, such that said organic matter reacts with said oxidizing agent, said oxidizing agent being present in an amount such that an excess of said oxidizing agent is left unreacted;
    (b) permitting an enzyme-catalyzed release of oxygen from said excess; and
    (c) measuring the volume of oxygen produced in step (b); whereby the volume of oxygen provides a measure of the reaction between the organic matter and oxidizing agent.

2. The method of claim 1, wherein said release of oxygen in step (b) is catalyzed by an immobilized enzyme, said release of oxygen further being enabled by contacting the resulting mixture from step (a) with said immobilized enzyme.

3. The method of claim 1, wherein said sample of fluid is acidified prior to reaction with said oxidizing agent.

4. The method of claim 1, wherein said sample of fluid is pre-prepared prior to step (a), said pre-preparation selected from the group consisting of (1) homogenization and (2) heat treatment.

5. The method of claim 1, wherein step (a) is continued until substantially all organic matter present in said sample of fluid has reacted with said oxidizing agent.

6. The method of claim 1, in which step (a) includes the substep of accelerating said reaction.

7. The method of claim 6, wherein said accelerating substep is enabled by an accelerant selected from the group consisting of (1) ultra-violet light, (2) heat, and (3) the addition of metal ions.

8. The method of claim 1, wherein step (a) includes the substep of adding said oxidizing agent to said fluid in increments, the amount of each increment being controlled by data obtained from monitoring said volume of oxygen in step (c) in a feedback control mechanism.

9. The method of claim 8, wherein said feedback control mechanism comprises:
    means for reacting successively increasing amounts of said oxidizing agent according to step (a);
    means for monitoring an initial release of oxygen according to step (b); and
    means, responsive to said means for monitoring, for controlling said means for reacting.

10. The method of claim 1, wherein said fluid includes viable aerobic cells, and wherein the content of organic matter in said fluid corresponds to the viable aerobic cell content of said fluid.

11. The method of claim 10, further comprising the step of chemically disrupting the integrity of said cells, either (1) prior to, or (2) coincident with, step (a).

12. The method of claim 10, further comprising the step of physically disrupting the integrity of said cells, either (1) prior to, or (2) coincident with, step (a).

13. The method of claim 10, wherein said release of oxygen in step (b) is catalyzed by an enzyme present in said viable aerobic cells.

14. The method of claim 1, wherein said release of oxygen in step (b) is catalyzed by enzyme selected from the group consisting of (1) peroxidase and (2) catalase.

15. The method of claim 1, wherein said oxidizing agent is hydrogen peroxide.

16. The method of claim 15, wherein said hydrogen peroxide is provided as a liquid.

17. The method of claim 1, further comprising the step of maintaining all reactants in steps (a) and (b) at a temperature not substantially less than biological temperature.

18. The method of claim 1, wherein oxygen measurement in step (c) is enabled using a pressure transducer.

19. The method of claim 18, wherein said pressure transducer is a low-flow gas meter.

20. The method of claim 1, wherein oxygen measurements in step (c) are processed by a data acquisition system.

* * * * *